(12) United States Patent
Cottone

(10) Patent No.: US 11,338,111 B2
(45) Date of Patent: May 24, 2022

(54) VASCULAR RE-ENTRY CATHETER

(71) Applicant: ORBUSNEICH MEDICAL PTE. LTD., Singapore (SG)

(72) Inventor: Robert J. Cottone, Davie, FL (US)

(73) Assignee: ORBUSNEICH MEDICAL PTE. LTD., Singapore (SG)

( * ) Notice: Subject to any disclaimer, the term of this patent is extended or adjusted under 35 U.S.C. 154(b) by 198 days.

(21) Appl. No.: 16/594,941

(22) Filed: Oct. 7, 2019

(65) Prior Publication Data

US 2020/0046944 A1 Feb. 13, 2020

Related U.S. Application Data

(63) Continuation of application No. 14/854,242, filed on Sep. 15, 2015, now abandoned.

(60) Provisional application No. 62/060,152, filed on Oct. 6, 2014, provisional application No. 62/050,456, filed on Sep. 15, 2014.

(51) Int. Cl.
*A61M 25/01* (2006.01)
*A61M 25/00* (2006.01)
*A61B 17/22* (2006.01)
*A61B 90/00* (2016.01)

(52) U.S. Cl.
CPC .... *A61M 25/0194* (2013.01); *A61M 25/0068* (2013.01); *A61B 2017/22095* (2013.01); *A61B 2090/3966* (2016.02); *A61M 25/0108* (2013.01); *A61M 25/0138* (2013.01); *A61M 2025/0197* (2013.01)

(58) Field of Classification Search
CPC .......... A61M 25/0194; A61M 25/0068; A61M 25/0108; A61M 25/0138; A61M 2025/0197; A61B 2090/3966; A61B 2017/22095
See application file for complete search history.

(56) References Cited

U.S. PATENT DOCUMENTS

| 5,429,617 | A | 7/1995 | Hammersmark et al. |
| 5,788,680 | A | 8/1998 | Linder |
| 7,632,241 | B2 | 12/2009 | Raijman et al. |
| 8,202,246 | B2 | 6/2012 | Kugler |

(Continued)

FOREIGN PATENT DOCUMENTS

| CN | 103702626 A | 4/2014 |
| GB | 2552924 A | 2/2018 |

(Continued)

OTHER PUBLICATIONS

Chinese Office Action issued in corresponding Chinese Application CN 201580059919.0, dated Jul. 19, 2019, with English translation.

(Continued)

*Primary Examiner* — Richard G Louis
(74) *Attorney, Agent, or Firm* — Leason Ellis LLP

(57) ABSTRACT

A catheter has a guide-tip including at least one wing for crossing a CTO lesion in an artery via exploring the subintimal space. The catheter can includes one or more exit port(s) and radiopaque marker(s) for steering a re-entry wire through one of the exit ports. The catheter may include a number of spiral-cut sections with varying characteristics to provide different strength and flexibility along the axial direction.

15 Claims, 17 Drawing Sheets

(56) References Cited

U.S. PATENT DOCUMENTS

| | | | |
|---|---|---|---|
| 2004/0243104 A1 | 12/2004 | Seddon | |
| 2005/0042448 A1* | 2/2005 | Bullen | B32B 25/14 |
| | | | 428/375 |
| 2005/0059990 A1 | 3/2005 | Ayala et al. | |
| 2006/0199147 A1 | 9/2006 | Mahlmann | |
| 2006/0200110 A1* | 9/2006 | Lentz | A61M 25/0662 |
| | | | 604/524 |
| 2008/0262472 A1* | 10/2008 | Lunn | A61M 25/0012 |
| | | | 604/527 |
| 2009/0054825 A1 | 2/2009 | Melsheimer et al. | |
| 2010/0063534 A1 | 3/2010 | Kugler et al. | |
| 2011/0054448 A1 | 3/2011 | Bourne et al. | |
| 2011/0098683 A1 | 4/2011 | Wiita et al. | |
| 2011/0313399 A1 | 12/2011 | Jacoby et al. | |
| 2012/0101510 A1 | 4/2012 | Lenker et al. | |
| 2013/0072957 A1 | 3/2013 | Anderson | |
| 2013/0317528 A1 | 11/2013 | Anderson et al. | |
| 2014/0165357 A1 | 6/2014 | Racz | |
| 2014/0171826 A1 | 6/2014 | Lampropoulos et al. | |
| 2016/0074627 A1 | 3/2016 | Cottone | |
| 2018/0056046 A1 | 3/2018 | Kiersey et al. | |
| 2018/0333162 A1 | 11/2018 | Saab | |

FOREIGN PATENT DOCUMENTS

| | | |
|---|---|---|
| JP | 2003-509176 A | 3/2003 |
| JP | 2010-531670 A | 9/2010 |
| JP | 2010509994 | 4/2011 |
| JP | 2011510795 | 4/2011 |
| WO | 95/26776 | 10/1995 |
| WO | 01/021249 A1 | 3/2001 |
| WO | 2007/145796 A2 | 12/2007 |
| WO | 2008/120209 A1 | 10/2008 |
| WO | 20090054943 | 4/2009 |
| WO | 2009100129 | 8/2009 |
| WO | 2013/022525 A1 | 2/2013 |
| WO | 2017/132573 A1 | 8/2017 |

OTHER PUBLICATIONS

Final Rejection issued in corresponding Japanese Application JP 2017-514549, dated Sep. 3, 2019, with English translation.

International Search Report and Written Opinion dated Jan. 27, 2016 corresponding to International Patent Application No. PCT/US2015/50092; 17 pages.

European Search Report corresponding to European Patent Application No. EP15841806 dated May 16, 2018.

Non-Final Japanese Office Action corresponding to Japanese Patent Application No. 2017-514549 dated Feb. 5, 2019, with translation.

International Search Report and Written Opinion of International Application PCT/US20/57640, dated Mar. 10, 2021.

International Search Report and Written Opinion of International Application PCT/IB2020/060143, dated Mar. 4, 2021.

International Search Report and Written Opinion of International Application PCT/IB2020/060145, dated Mar. 3, 2021.

* cited by examiner

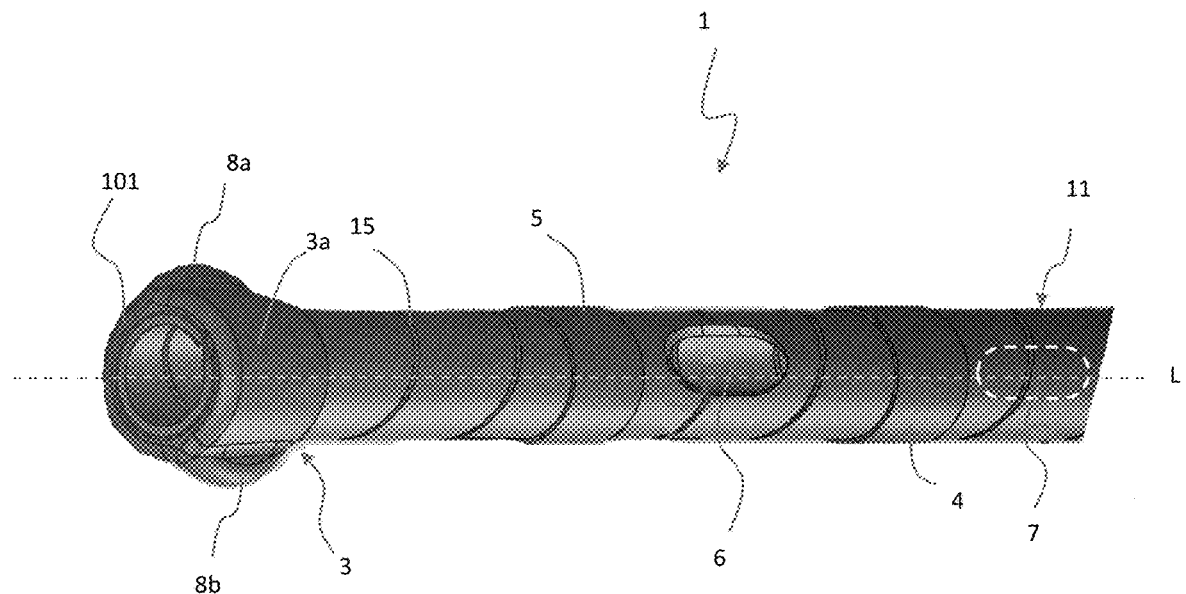
Figure 2A
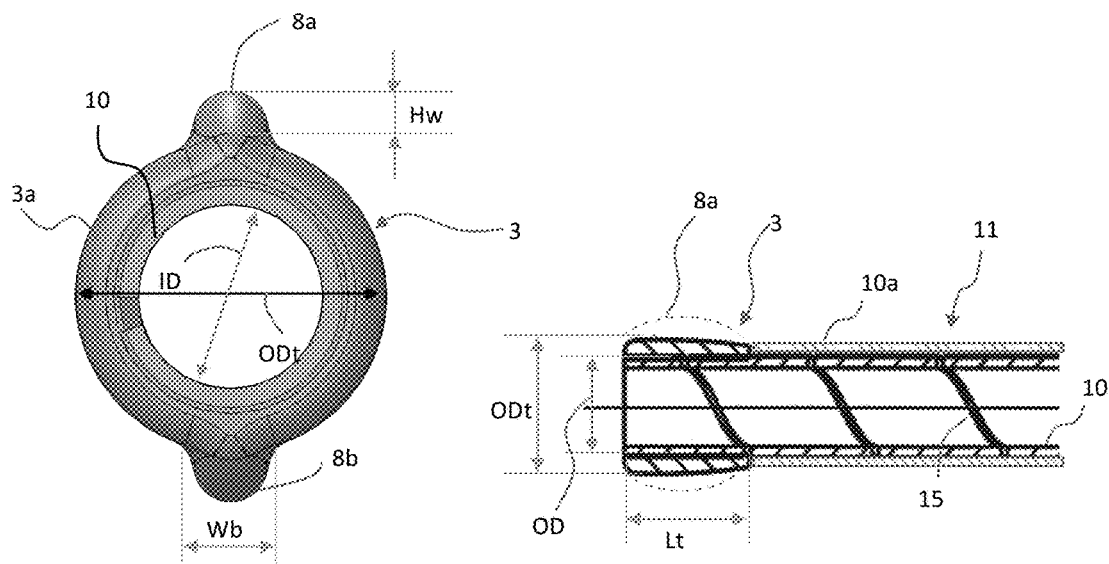
Figure 2B
Figure 2C

VASCULAR RE-ENTRY CATHETER

CROSS REFERENCES TO RELATED APPLICATIONS

This application is a Continuation of U.S. patent application Ser. No. 14/854,242, filed Sep. 15, 2015, which claims priority to U.S. provisional application Nos. 62/050,456 (filed Sep. 15, 2014) and 62/060,152 (filed Oct. 6, 2014), the disclosure of each of which is incorporated by reference in their entirety.

BACKGROUND

Chronic Total Occlusion ("CTO") is a complete or near complete blockage of a blood vessel, such as a coronary artery. As many as 30% of the patients with coronary artery disease have CTOs somewhere through the left or right arterial system. Traditionally CTO has usually been treated by a bypass procedure where an autologous or synthetic blood vessel is anastomotically attached to locations on the blood vessel upstream and downstream of the occlusion. While effective, such bypass procedures are quite traumatic to the patient.

Recently, catheter-based intravascular procedures have been developed to treat CTO with improved success rates. Such procedures include angioplasty, atherectomy, stenting, and the like, and the catheters are usually introduced percutaneously. Treatment of CTO percutaneously significantly reduces the need for surgery (coronary artery bypass graft—CABG). Moreover, CTO percutaneous coronary intervention (PCI) can result in symptomatic relief for the patient, re-establishing coronary blood flow, improved left ventricular function and potentially, survival advantage. Peripheral vascular occlusions outside of the coronary vascular anatomy are also treatable with such interventions.

Before such catheter-based treatments can be performed, it is usually necessary to cross the occlusion with a guidewire to provide access for the interventional catheter. Available techniques for crossing the occlusion generally fall into two approaches: the antegrade approach, which involves crossing a wire from the proximal end to the distal end of the occlusion (either through the CTO directly or through the subintimal space), and the retrograde approach, which refers to CTO access of the distal cap via collateral vessels. The latter is usually reserved as a second line strategy for failed intimal antegrade crossing.

For treating CTO by PCI with antegrade access, a number of different devices have been developed, including the CrossBoss™ and Stingray™ systems. See http://www.bostonscientific.com/en-US/medical-specialties/interventional-cardiology/procedures-and-treatments/coronary-chronic-total-occlusion-system.html (last accessed Sep. 10, 2015); see also, U.S. Pat. Nos. 8,632,556, 8,202,246, 8,636,712, 8,721,675, 6,511,458.

The CrossBoss™ catheter can be first used to facilitate the crossing a CTO as simply bluntly dissecting via small micro channels within the vessel through the occlusion or if this is not successful in crossing, the device can navigate from the subintimal space of a vascular wall. As an illustration, FIG. 1A shows a schematic representation of a CrossBoss™ catheter 100, which includes a rounded/blunt distal tip 108 mounted to a flexible proximal shaft 120 which is torquable through rotation of the handle 130, the shaft 120 having a lumen which accommodates a guidewire 102.

The Stingray™ catheter, Stingray™ Guidewire can be used subsequent to the CrossBoss™ catheter to facilitate orienting and steering a guidewire or reentry device from the subintimal space into the true lumen of an artery. As an illustration, FIG. 1B shows a schematic representation of a Stingray™ catheter having a distally positioned laterally inflatable balloon 210 and a proximal shaft 220 having a central guidewire lumen 225. The side-ports 212 and 214 are located on opposite sides of a portion of the central lumen flanked by the balloon 210 and identified by radiopaque markers 232 and 234. The side ports 212 and 214 communicate with the central guidewire lumen 225 and facilitate the steering of the reentry device 240 with a pre-biased tip (at an angle to the central lumen) by allowing the tip of the Stingray™ Guidewire reentry device 240 to exit from the catheter from one of the side ports.

The CrossBoss™ catheter can be used to pass through the proximal cap of a CTO by rotation of the blunt tip. However, if this is not successful, a procedure employing both the CrossBoss™ and Stingray™ catheters to cross the CTO would be needed. The procedure can be generally described as follows.

(1) advancing the CrossBoss™ catheter over a guidewire to an interface between the catheter distal tip and surrounding tissue;

(2) penetrating the catheter tip into the vascular wall and advancing the CrossBoss™ device within the vascular wall to establish a channel in the subintimal space of the vascular wall such that the tip extends longitudinally across the occlusion;

(3) withdrawing the CrossBoss™ catheter over the guidewire;

(4) advancing the Stingray™ catheter over the guidewire;

(5) inflating the balloon of the Stingray™ catheter to cause the Stingray™ balloon to assume one of two orientations;

(6) withdrawing the guidewire from the Stingray™ catheter;

(7) advancing a reentry device having a pre-configured tip portion in a compressed state into the lumen of the Stingray™ catheter; and (8) manipulating the tip of the reentry device with the aid of radiographic visualization such that the tip of the reentry device exits from one side port of the Stingray™ catheter in a natural state and into the lumen of the artery (true lumen).

The Stingray™ catheter can then be withdrawn, leaving the reentry device in place which establishes a pathway from the proximal segment of the vascular lumen and the distal segment of the vascular lumen, over which a balloon catheter can be subsequently introduced and deployed at the site of the CTO. A stent can be further implanted at the site which has been expanded by the balloon.

While the above procedure of subintimal crossing using a combination of CrossBoss™ and Stingray™ catheters overcame certain difficulties of previous generation techniques in direct antegrade CTO access, the procedure is complex and time-consuming. Furthermore, switching from CrossBoss™ to Stingray™ can introduce unintended errors. For example, withdrawing the CrossBoss™ catheter from the guidewire (so that the Stingray™ catheter may be introduced over the guidewire) may cause the guidewire to shift position in the subintimal space, or worse, to retract from the subintimal space, in which case the operator would not be able to properly introduce the Stingray™ catheter over the guidewire into the subintimal space. As a result, the previous step of using CrossBoss™ catheter to cross the subintimal space would need to be repeated. Additionally, advancing and inflating the distal balloon of the Stingray™ catheter in the subintimal space can create excessive delamination and substantial trauma in the layers of the vascular wall.

It would be desirable to provide devices and methods for treatment of vascular conditions associated by crossing a CTO in a blood vessel by exploring the subintimal space in a more simplified procedure with reduced error rate and reduced trauma to the blood vessel.

SUMMARY OF THE INVENTION

In one aspect, the present invention provides a catheter device. The catheter device includes a distal catheter tube portion having a longitudinal axis and including a tube wall comprising at least one side port, at least one radiopaque marker, and at least one wing protruding radially outward from the tube wall.

In some embodiments, the tube wall includes two wings protruding radially outward in diametrically opposing directions. In certain of these embodiments, wherein the at least one side port is radially offset from each of the two wings for about 90 degrees. In specific embodiments, the first side port and the second side port are radially offset for about 180° degrees from each other.

In some embodiments, the at least one side port is beveled.

In some embodiments, the catheter device includes a radiopaque marker affixed on the distal catheter tube portion in axial alignment with the at least one side port. In other embodiments, the catheter device includes a radiopaque marker encircling the at least one side port.

In some embodiments, the tube wall includes a first side port and a second side port which is longitudinally and radially offset from the first side port, the second side port being located distal the first side port. In certain of these embodiments, the tube wall comprises a first radiopaque marker located longitudinally between the first side port and the second side port, and a second radiopaque marker distal the second side port.

In some embodiments, the at least one wing is part of a guide-tip engaging a distal end of the catheter. In other embodiments, the at least one wing can be placed in a distance from the distal end of the catheter.

In some embodiments, the catheter device includes at least one spiral-cut section, and the at least one side port is located in the spiral-cut section.

In certain embodiments, the catheter device includes at least two spiral-cut sections having different pitches.

In some embodiments, the catheter device includes at least one spiral-cut section with interrupted spirals.

In certain embodiments, the catheter device includes at least two interrupted spiral-cut sections having different pitches.

The at least one wing can be formed from a polymeric material, a metal, or a composite material.

In another aspect, the present invention provides a method for facilitating treatment of an occlusion in a blood vessel with a catheter device as described herein. The blood vessel has a vascular wall defining a vascular lumen containing an occlusion therein. The occlusion separates the vascular lumen into a proximal segment and a distal segment. The catheter device has a lumen and includes a distal catheter tube portion including a tube wall comprising at least one side port and at least one radiopaque marker, and a guide-tip located at a distal end of the catheter, where the guide-tip includes at least two wings protruding radially outward in diametrically opposing directions. The method includes: positioning the catheter device proximate the occlusion; advancing the guide-tip within the vascular wall adjacent the occlusion until the at least one side port is positioned distal of the occlusion to establish a channel in the vascular wall extending longitudinally across the occlusion; orienting the at least one side port toward the vascular lumen; inserting a re-entry device through the lumen of the catheter device wherein the re-entry device has a distal end portion in a compressed state; and manipulating the re-entry device such that a distal end portion of the re-entry device exits, in a natural state, from the at least one side port into the distal segment of the vascular lumen.

BRIEF DESCRIPTION OF THE DRAWINGS

FIG. 2A shows a catheter (tube) having a guide-tip with wings, and a side port in a spiral-cut section according to one embodiment of the present invention.

FIG. 2B shows a front view of the guide-tip of the catheter shown in FIG. 2A.

FIG. 2C is a side cross section view of a portion of the catheter shown in FIG. 2A.

DETAILED DESCRIPTION

Figure 1A:
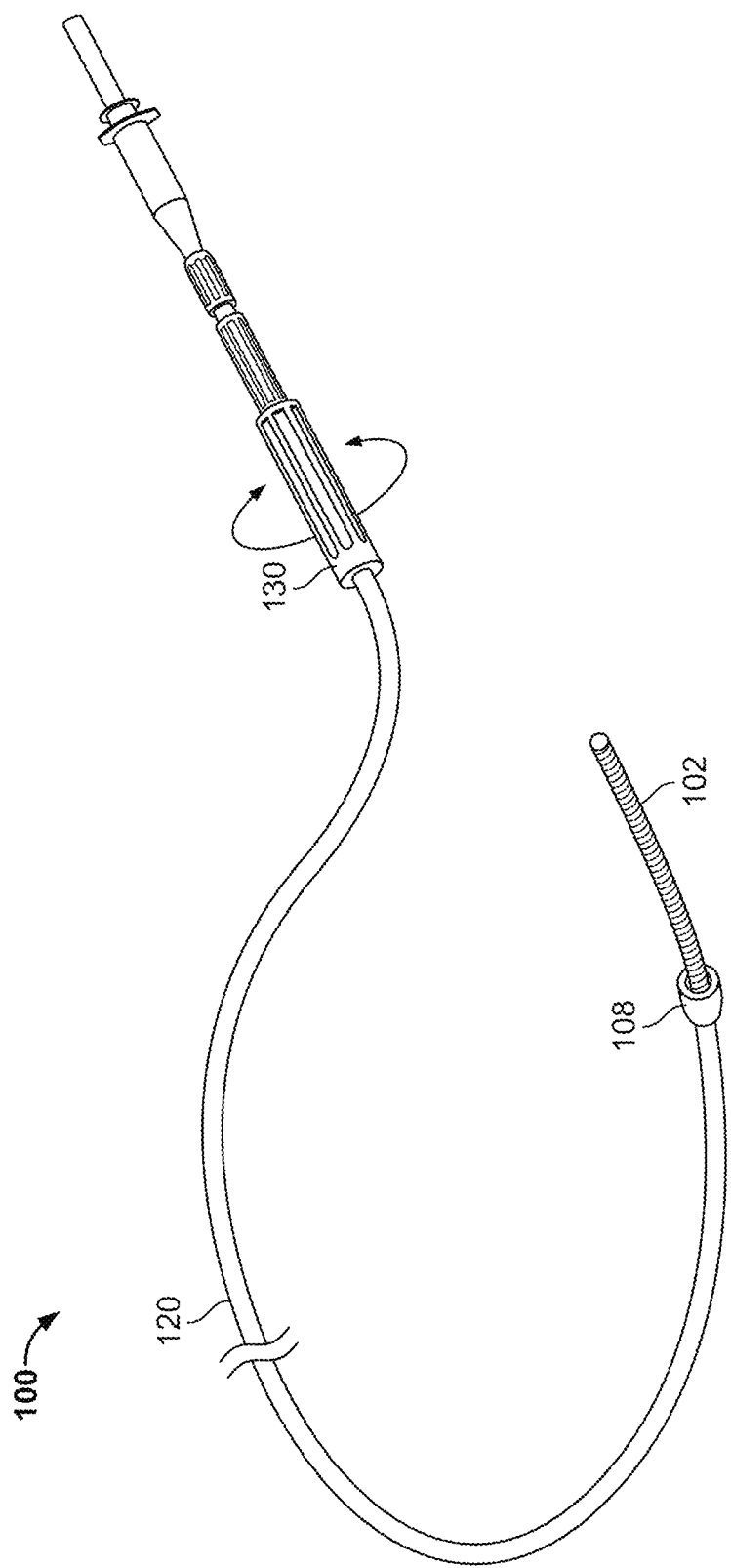
FIG. 1A schematically depicts a CrossBoss™ catheter which is known in the art.
Figure 1B:
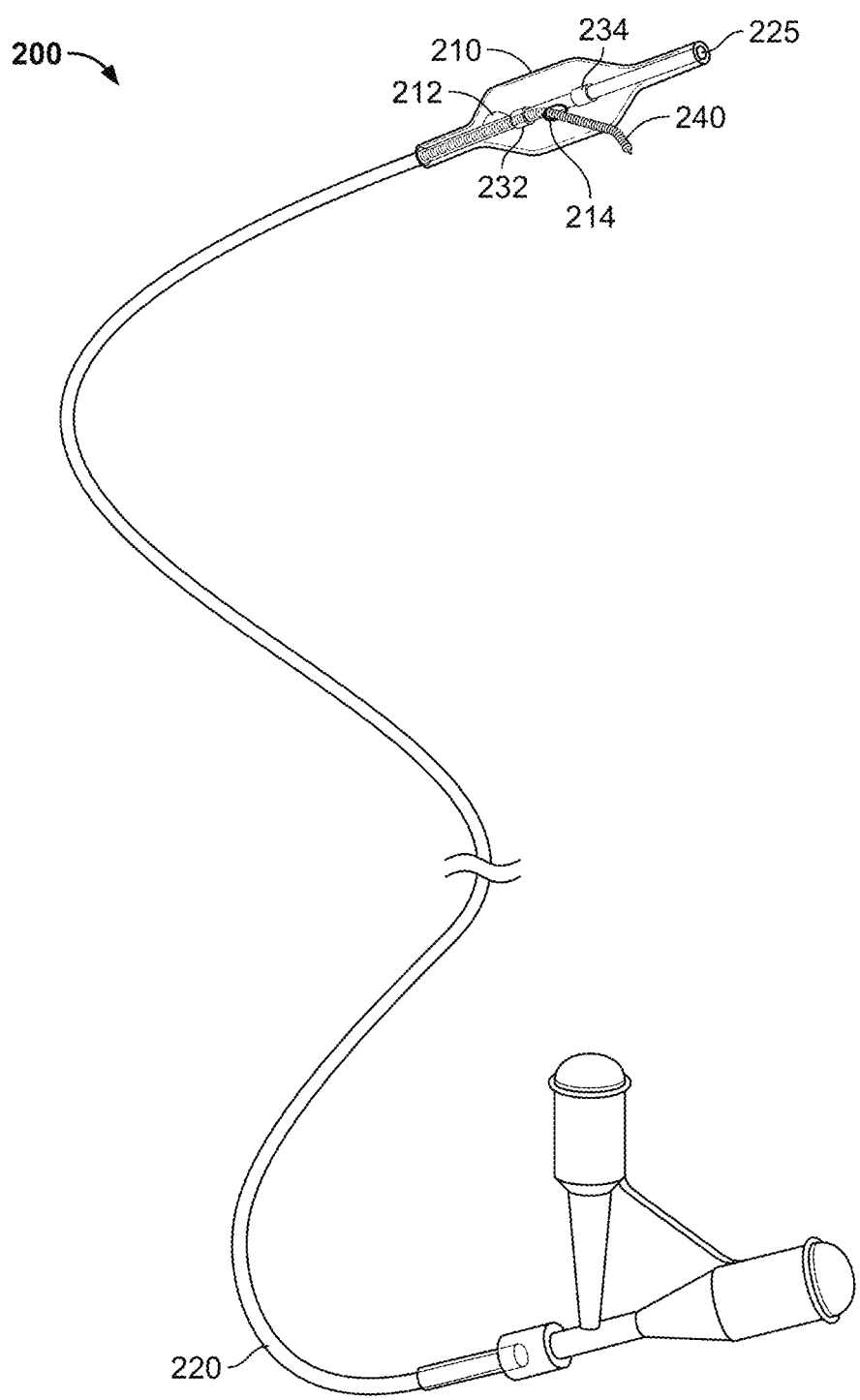
FIG. 1B schematically depicts a Stingray™ catheter which is known in the art.

In one aspect, the present invention provides a catheter device (or catheter). The catheter can be used for the treatment of CTO, either by passing the CTO directly, or by passing the CTO via the subintimal space. In another aspect, the present invention provides a method for treating CTO.

As illustrated in FIGS. 2A and 2B, a catheter device 1 according to one embodiment of the present invention includes a distal tube portion 11 having a tube wall 10 and a longitudinal axis L. On the distal end 101 of the catheter 1 (which is also the distal end of the distal tube portion 11) is a blunt guide-tip (or tip) 3, which encircles a distal end portion of the distal tube portion 11. Guide-tip 3 includes a base portion 3a, as well as two lateral wings 8a and 8b radially protruding outward from the circumference of tip 3. In certain embodiments, the guide-tip 3 wing can include fewer or more wings, e.g., only one wing, or greater than two wings, as described herein.

When two wings are present, they can be radially separated or offset by an angle of about 30 to about 90 degrees, or from about 90 to about 180 degrees or any fraction in-between. For example, the angle can be about 30 degrees, about 60 degrees, about 90 degrees, about 120 degrees, about 150 degrees or about 180 degrees. As shown in FIGS. 2A and 2B, in some embodiments, the two wings 8a and 8b can be positioned approximately diametrically opposed around the guide-tip, i.e., about 180 degrees from each other ±10 degrees, more preferably ±5 degrees.

FIG. 2C shows a cross section view of a portion of the tube 1 of FIG. 2A along the longitudinal axis L. As shown in FIGS. 2B and 2C, the outer diameter of the guide-tip ODt (which does not include the wings) is greater than the outer diameter (OD) of the distal tube portion 11, which is greater than the inner diameter (ID) of the distal tube portion 11. The wings have a base width Wb, a height Hw measured from OD to the peak of the wings. The leading edges of the wings are generally rounded or smooth.

Figure 2D:
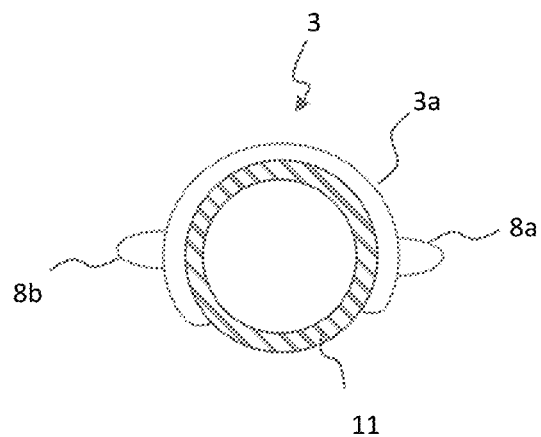
FIG. 2D is a front view of a guide-tip with wings according to one embodiment of the present invention.
Figure 2E:
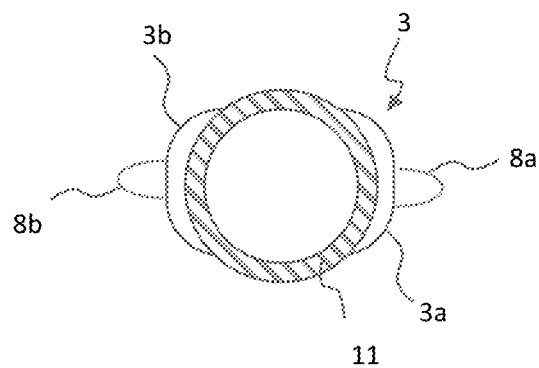
FIG. 2E is a front view of a guide-tip with wings according to another embodiment of the present invention.

As shown in FIG. 2B, the guide-tip 3 can, in certain embodiments, completely encircle a circumference of distal tube portion 11. In alternative embodiments, and as illustrated in FIGS. 2D and 2E, the guide-tip 3 (including base 3a and wings 8a/8b) does not completely encircle of the distal tube portion 11. For example, the guide-tip 3 only encircles three quarters, two thirds, one quarter or smaller percentages of the circumference of the distal tube portion 11. In certain embodiments, and as illustrated in FIG. 2E, the guide-tip 3 may include multiple separate base parts (3a, 3b) distributed along the circumference of the distal tube portion 11.

In certain embodiments, the guide-tip 3 with wings 8a and 8b may be positioned slightly away from the distal end 101 of the tube portion 11, e.g., at a distance dw ranging from about 1 to about 100 mm (see FIG. 2F), e.g., about 10 mm to about 75 mm, or about 25 to about 50 mm.

In certain embodiments, one or more wings can be directly joined to the tube without being supported by a base portion of a tip, e.g., at the distal end 101, and/or away from the distal end 101. As illustrated in FIG. 2G, wings 8a/8b are directly joined to the tip of the distal tube portion 11 (e.g., by welding, adhering, etc.) without being a part of a tip encircling a distal tube portion 11. In such situations, the wing(s) itself can also be considered as the only component of a guide-tip.

Depending on the material as well as the structural requirements in terms of flexibility, the thickness of the tube wall 10 can vary, e.g., from about 0.002 inch to about 0.02 inch, or from about 0.05 mm to 2 mm, e.g., 0.05 mm to about 1 mm, about 0.1 mm, 0.2 mm, 0.3 mm, 0.4 mm, 0.5 mm, 0.6 mm, 0.7 mm, 0.8 mm, 0.9 mm, 1.0 mm, etc. The inner diameter of the lumen (ID) of the distal tube portion 11 can vary, e.g., from about 0.01 inch to about 0.04 inch, or from about 0.1 mm to about 2 mm, or from about 0.25 mm to about 1 mm, e.g., about 0.2 mm, about 0.3 mm, about 0.4 mm, about 0.5 mm, about 0.6 mm, about 0.7 mm, about 0.8 mm, about 0.9 mm, about 1 mm, etc. The outer diameter of the lumen (OD) of the distal tube portion can also vary, e.g., from about 0.2 mm to about 3 mm, e.g., about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, etc. The thickness of the tube wall, the inner diameter ID and the outer diameter OD can each be constant throughout the length of the catheter, or vary along the length of the catheter.

In certain embodiments, the height of the wings Hw can range from about 5%-about 50% (including about 10% to about 40%, about 15% to about 30%, or about 20%) of the outer diameter ODt of the tip 3; alternatively, the height of the wings Hw can be about 10% to about 15%, about 15% to about 30%, or about 5% to about 45% of ODt. In some embodiments, the base width of the wings Wb can be about 5%-30% of the outer diameter ODt of the tip 3. The axial length of the base of the wings can be approximately the same as the axial length Lt of the guide-tip 3 (see FIG. 2C), and can range from about 5 mm to about 20 mm, about 7.5 mm to about 15 mm, about 8 mm to 12 mm, or about 10 mm. Alternatively, the axial length of the base of the wings can be smaller than the axial length Lt of the guide-tip 3.

The tube wall 10 and guide-tip 3 may be formed from a metal, a polymer or a composite material. Suitable metals can include cobalt-chromium, stainless steel, MP35N, nickel titanium, etc., as well as metal alloy such as a shape memory material, e.g., Nitinol. Alternatively, the tube wall may be composed of polymers such as aliphatic polyether-urethanes, polyamides, low-density polyethylene (LDPE), polypropylene or mixtures of polymers. The tube wall distal tube portion may also be formed from a composite of polymers and metal, such as a composition of joined or abutted metal and polymer forming a generally tube like structure. The distal catheter tube portion can be formed from metal, e.g., stainless steel. The guide-tip 3 and/or the wings 8a/8b can be made of the same material as the tube wall or different materials. For example, the guide-tip may include a radiopaque material such as a radiopaque filler composition. The guide-tip may include metal and a softer outer component such as a polymer varying in udometer from soft rubber like materials to hard composite polymer or plastics. Also, the wings may be made from the same or different material as the remainder of the guide-tip. For example, the wings may be formed from a polymeric material, a shape memory material such as Nitinol, or a metal such as cobalt chromium.

Figure 3A:
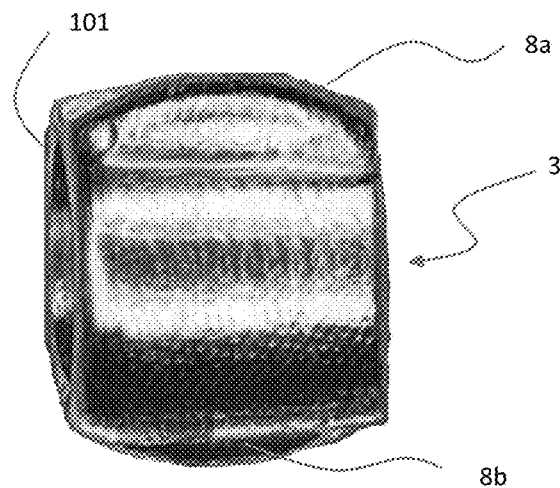
FIG. 3A is a photo of a guide-tip as illustrated in FIGS. 2A and 2B.
Figure 3B:
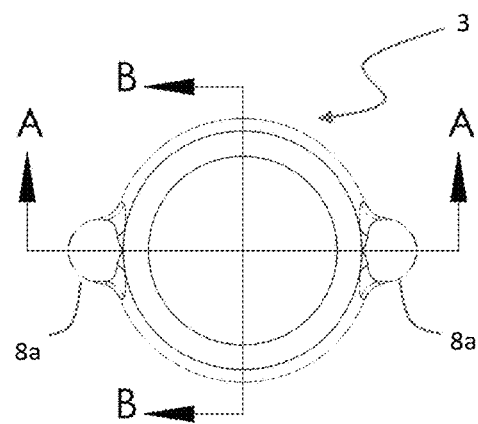
FIG. 3B is a back view of the guide-tip as illustrated in FIGS. 2A and 2B.
Figure 3C:
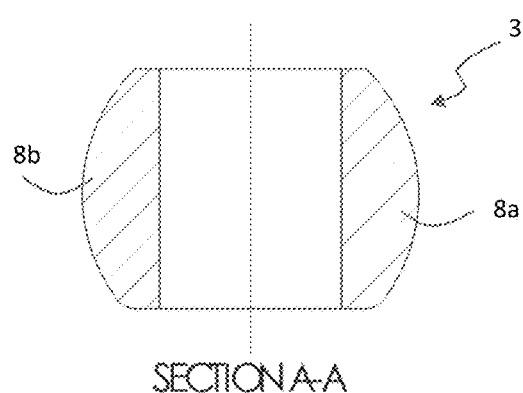
FIGS. 3C and 3D are cross section views of the guide-tip along lines A-A and B-B indicated in FIG. 3A.
Figure 3D:
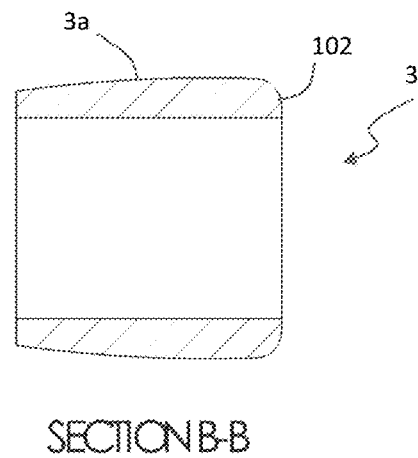
Figure 3E:
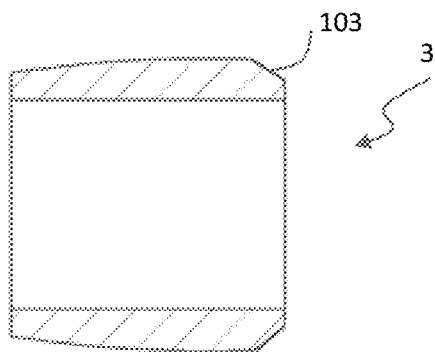
FIG. 3E is a cross section view of a guide-tip according to another embodiment of the present invention.

FIG. 3A shows a photomicrograph of the guide-tip 3 including two wings 8a and 8b extending from the top and bottom, respectively. The left side of the guide-tip 101 can be engaged to a distal end of a catheter as described previously. FIG. 3B shows a back view of the guide-tip. FIG. 3C is a sectional view along A-A line in FIG. 3B (through the wings 8a/8b). FIG. 3D is a cross sectional view along B-B line in FIG. 3B, showing that the base portion of tip 3 has a rounded leading edge 102. The leading edge can alternatively include a taper 103, as shown in FIG. 3E which may be smooth, i.e., have no sharp, cutting edges, enabling controlled blunt micro dissection.

Figure 3F:
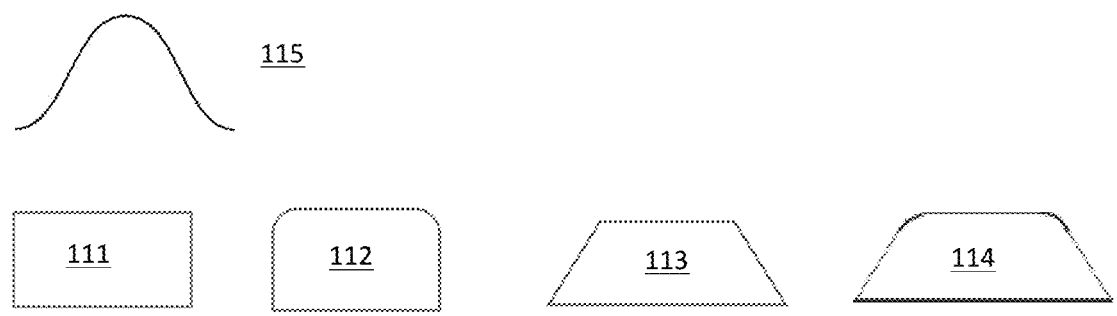
FIG. 3F shows exemplary side cross section wing shapes according to some embodiments of the present invention.

The peripheral contour of the wings along the axial direction can be generally convex in shape, e.g., in the shape of a smooth elliptical curve (see FIG. 2A/2C/3A/3C). In other embodiments, and as illustrated in FIG. 3F, the side profile or shape of the wings may be rectangle (111), trapezoidal (113), or rectangular or trapezoidal with rounded outer corners (112 and 114, respectively), or sinusoidal (115).

Figure 3G:
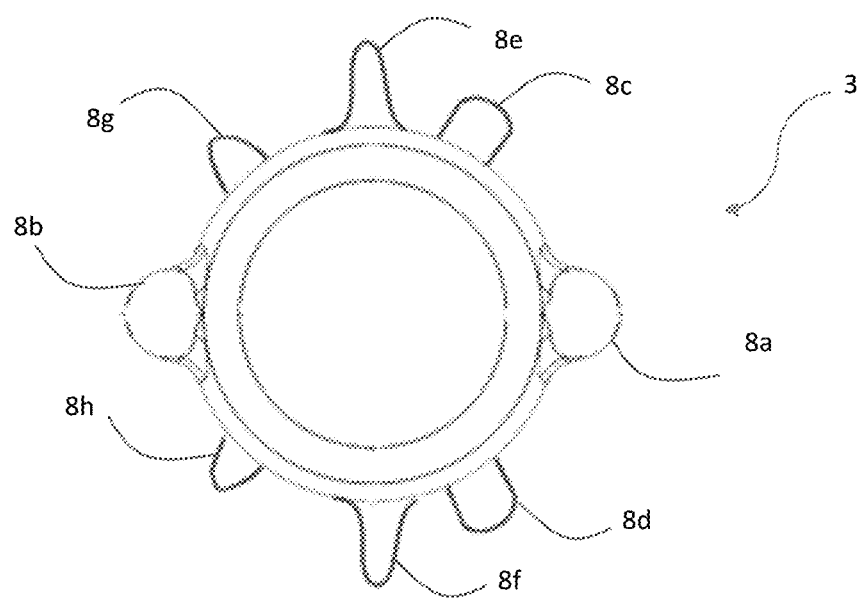
FIG. 3G is a front view of a guide-tip having more than two wings according to some embodiments of the present invention.

More than two wings may be positioned around a circumference of the guide-tip 3. For example, a plurality of wings may be positioned evenly or unevenly along the circumference, and they can be arranged symmetrically or asymmetrically. The plurality of wings may be identical or different in shape and/or size. As shown in FIG. 3G, 8 wings (8a, 8b, 8c, 8d, 8e, 8f, 8g, 8h) are disposed at or near the distal end of the distal tube portion. The transverse cross sections of these wings (perpendicular to the axial direction of the distal tube portion) can vary in size and shape as shown (e.g., generally bell shape, arc, rectangle with rounded corners, etc.), where the exterior surfaces of the wings usually form a smooth transition with the outer wall of the tip.

Figure 3H:
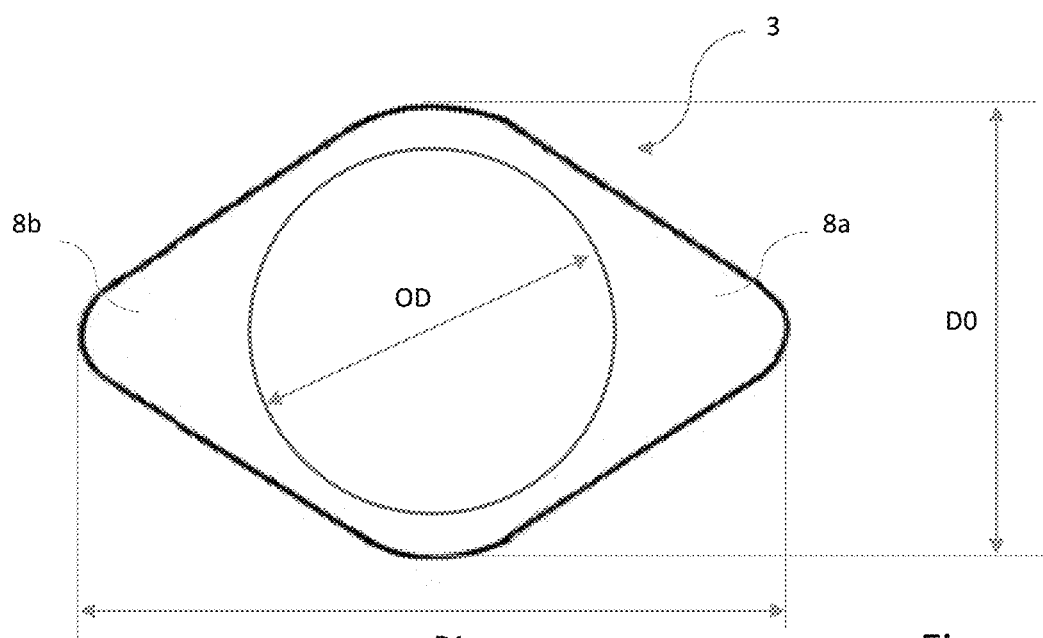
FIG. 3H is a front view of a guide-tip having an anisotropic transverse cross section shape according to some embodiments of the present invention.

In certain embodiments, the wings may form a continuous line with a base portion of the guide-tip. For example, as illustrated in FIG. 3H, which is a front view of a guide-tip 3, the wings 8a and 8b of tip 3 protruding laterally due to the anisotropic transverse cross sectional shape of guide-tip 3. In such embodiment, the, the maximum transverse cross sectional width of guide-tip 3, D1, (which can be considered a "wingspan") is greater than the minimum transverse cross sectional width of guide-tip 3, D0. For example, D1 can be greater than D0 for about 10% to about 500%, e.g., from about 50% to about 200%. In some embodiments, D1 can be about 10%, 20%, 50%, 80%, 100%, 150%, 200%, 250%, or 300% greater than that of the inner diameter of the tip (which is about equal to the outer diameter (OD) of the distal tube portion to which the guide-tip is to be engaged).

The guide-tip 3 (optionally with the wings) can be positioned on the distal end of the distal tube portion 11 by fusing or otherwise coupling the guide-tip 3 onto the tube wall 10. The wings can be fabricated as an integral part of tip 3; alternatively, the wings may be fused or otherwise coupled onto a base of tip 3 by a mechanical coupling (e.g., friction), adhesion, chemical linkage, etc.

The catheter 1 may be a micro catheter having one lumen for use in conjunction with a guiding catheter. The catheter 1 may also have more than one lumen, e.g., 2, 3, 4 or 5 lumens enclosed by the tube wall 10. The lumens may have equal or unequal inner diameters. One lumen may be connected to a balloon which can be affixed to the catheter 1. A steerable guidewire may be inserted through a lumen of the catheter. The catheter may be designed to optimize parameters such as push, torque, kink performance, trackability and transition. The wall thickness of the catheter may vary along its length direction, such that the flexibility of the catheter may vary along the length direction as needed or desired.

Figure 2F:
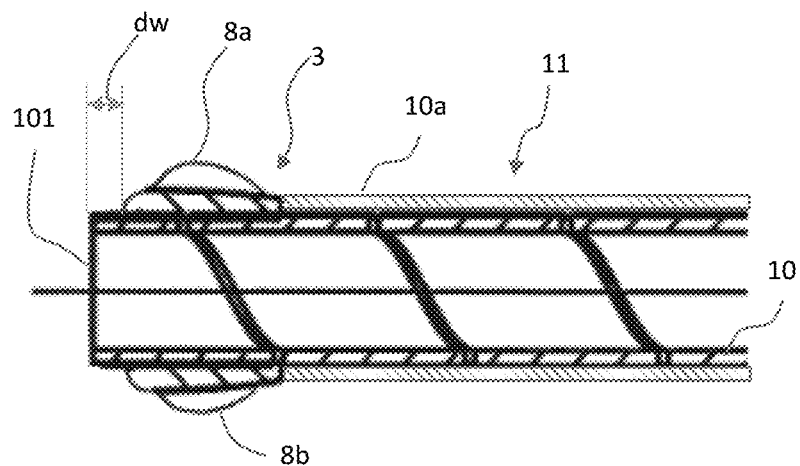
FIG. 2F is a side cross section view of a portion of a catheter having a winged guide-tip according to another embodiment of the present invention.
Figure 2G:
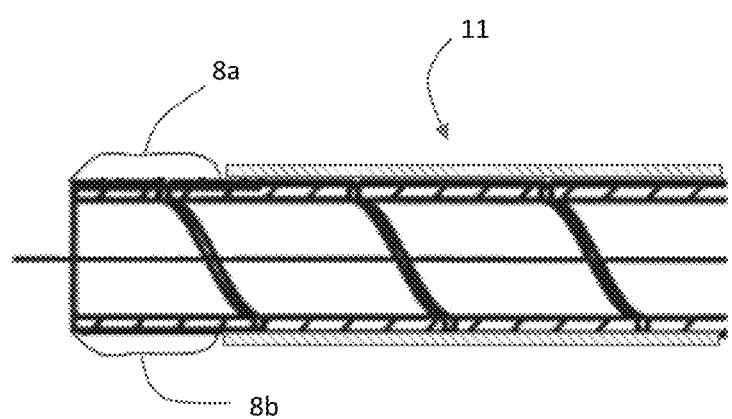
FIG. 2G is a side cross section view of a portion of a catheter having distal wings according to another embodiment of the present invention.

As shown in FIGS. 2C and 2F, the tube wall 10 may be covered by a protective jacket 10a to provide a smooth outer surface while not diminishing the flexibility of the distal tube portion 11. The jacket 10a can be made from a polymer, e.g., by enclosing the tube wall 10 with a co-extruded polymeric tubular structure of single of multiple layers and heat shrinking the tubular structure, or coating the tube wall 10 via a dip coating process. The polymer jacket material can be nylon, polyether block amide, PTFE, FEP, PFA, PET, PEEK, etc. Further, the distal tube portion 11 (or the entire length of catheter 1) may be coated with a hydrophilic polymer coating to enhance trackability. Hydrophilic polymer coatings can include polyelectrolyte and/or a non-ionic hydrophilic polymer, where the polyelectrolyte polymer can include poly(acrylamide-co-acrylic acid) salts, a poly(methacrylamide-co-acrylic acid) salts, a poly(acrylamide-co-methacrylic acid) salts, etc., and the non-ionic hydrophilic polymer may be poly(lactams), for example polyvinylpyrollidone (PVP), polyurethanes, homo- and copolymers of acrylic and methacrylic acid, polyvinyl alcohol, polyvinylethers, maleic anhydride based copolymers, polyesters, hydroxypropylcellulose, heparin, dextran, polypeptides, etc. See e.g., U.S. Pat. Nos. 6,458,867 and 8,871,869.

Also shown in FIG. 2A are two radiopaque markers 4 and 5 positioned along distal tube portion 11 for aiding radiographic visualization of the positioning of the catheter 1 in the vascular lumen. The markers can include a radiopaque material, such as metallic platinum, platinum-iridium, Ta, gold etc. in the form of wire coil or band, vapor deposition deposits, as well as radiopaque powders or fillers, e.g., barium sulfate, bismuth trioxide, bismuth sub carbonate, etc., embedded or encapsulated in a polymer matrix. Alternatively, the markers can be made from radiopaque polymers, such as radiopaque polyurethane. The markers can be in the form of bands to encircle the outer sheath of the distal tube portion 11, as shown in FIG. 2A.

As shown in FIG. 2A, the distal tube portion 11 between the marker 4 and marker 5 include a side port (or exit port) 6, which can be a through-hole on the tube wall 10. There may also be another side port 7 lying between guide-tip 3 and marker 5. (This side port can also be located proximal to marker 4). The side ports 6 and 7 can be used for exit of a re-entry wire or another re-entry device having a smaller diameter than that of the distal tube portion 11 at a direction deviating from the axis L of the distal tube portion 11. For example, the re-entry wire can have a pre-biased distal tip. As used herein, the term "pre-biased" when referring to a distal tip portion of a re-entry wire is meant that the tip portion of the re-entry wire can assume two different states, a compressed state and an uncompressed (or natural) state, where in the compressed state the distal tip portion can be axially aligned with the remainder of the wire, and in the uncompressed state the distal tip portion forms an angle (bent) with the remainder of the wire to facilitate the distal tip portion to exit from a side port of the catheter.

Side ports 6 and 7 can be positioned radially offset, between about 180° apart from each other, e.g., about 180° (±10°) apart from each other as shown in FIG. 2A. The radial displacement of the side ports relative to the wings may range from about 0° to 90°, e.g., 10, 20, 30, 50, 70 and 80 degrees. In one embodiment, the positions of the side ports may be radially offset from the wings at about 90°, as shown in FIG. 2A. In this way, when the two wings 8a/8b are positioned in a stable configuration in the subintimal space of an artery, port 6 can be facing either toward or opposing the true lumen of the artery, and the port 7 can face the opposite side.

The side ports may be symmetrical in shape and can be circular, semi-circular, ovoid, semi-ovoid, rectangular or semi-rectangular. The ports may have the same shape and size (i.e., surface area) or can be different from each other and are configured to allow for passage of a re-entry wire or another medical device through the ports. The dimensions of the port may be adjusted to accommodate different types of medical devices or wires, e.g., with diameters ranging from about 0.05 mm to about 1.0 mm. Erglis et al. *Eurointervention* 2010:6, 1-8. The distal tube portion 11 can contain more than two exit ports, e.g., 3, 4, 5, 6, 7, 8 . . . n ports along its length direction and radially distributed as desired.

Figure 4A:
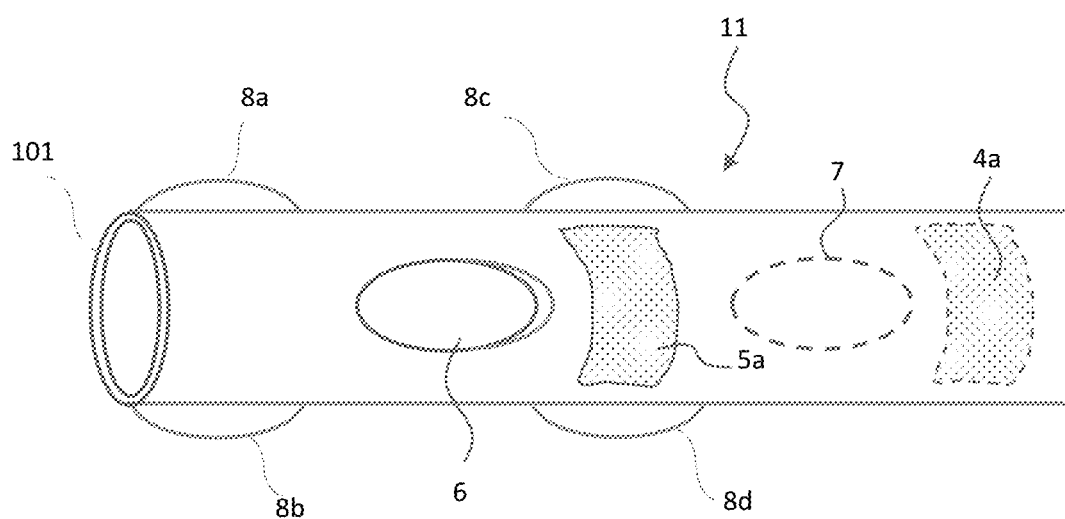
FIGS. 4A and 4B are schematic side views of a catheter having radiopaque markers according to some embodiments of the present invention.

The radiopaque markers configured as bands shown in FIG. 2A can be used to facilitate determination of the positions of the side ports while the distal tube portion 11 is maneuvered in a subject's anatomy. As shown in FIG. 4A, the markers 4a and 5a (marker 5a may be positioned on the opposite side of the tube 11 and therefore is hidden from the view as shown) can also be configured as a partial band or patch which form specific alignment with a corresponding side port. For example, as shown in FIG. 4A, marker 4a is axially aligned with side port 7, whereas marker 5a is axially aligned with side port 6. Thus, like the radially opposite configuration of the side ports 6 and 7, the markers 4a and 5a are also radially opposite to each other. In this manner, visualization of the markers 4a and 5a can be used to determine the orientation of the respective side ports. The markers can be configured in different shapes, e.g., partial circumferential bands, or any other desired shapes, to facilitate determination of orientation of the ports.

Figure 4B:
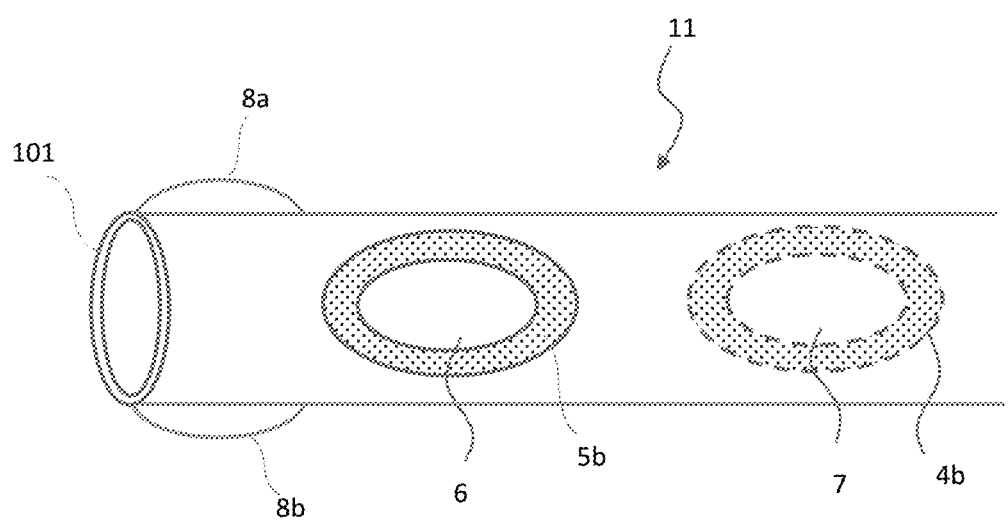

As shown in FIG. 4B, the markers can be configured as surface patches 4b (which is hidden from view and shown with dashed boundary line) and 5b that enclose the circumferences of the respective exit ports 7 and 6. In such an embodiment, the marker positions that can be visualized directly correspond to the side port positions.

In either FIG. 4A or 4B, the markers should have sufficient size and suitable configuration/construction (e.g., the type of radiopaque material, load amount of radiopaque material, etc.) such that they can be visualized with the proper radiographic aid.

Also shown in FIG. 4A are additional wings 8c and 8d, which are proximal to side port 6 (wings 8a and 8b are distal to side port 6). Radiopaque material can also be included in wings 8a, 8b, and/or 8c, 8d such that these wings can also serve as radiopaque markers to help visualize the positions of the side ports. Other configurations of radiopaque markers for determining the orientation of a catheter device can also be used. See WO2010092512A1, U.S. Pat. No. 8,983, 577, and U.S. Patent Application Publication No. 20140180068.

Figure 5A:
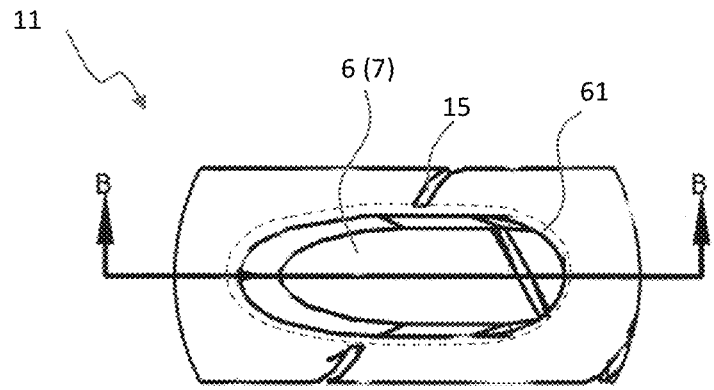
FIG. 5A is a top view of a beveled port on a spiral-cut section of a catheter according to one embodiment of the present invention.
Figure 5B:
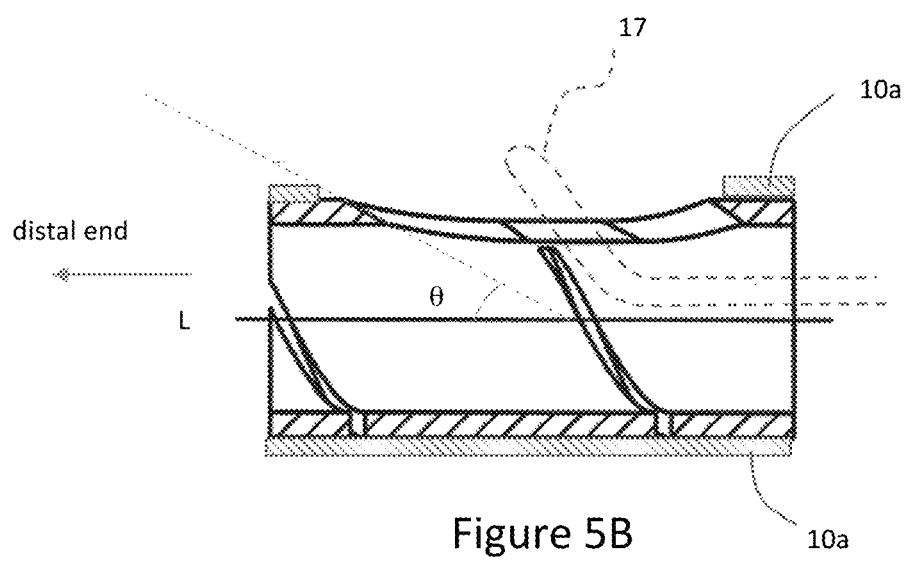
FIG. 5B is a side cross sectional view of the beveled port as shown in FIG. 5A.

In some embodiments, the side port 6 (or 7) may be beveled, as shown in FIG. 5A (perspective view) and FIG. 5B (side cross section view along line B-B in FIG. 5A). The beveled configuration of the side port can facilitate a re-entry wire 17 with a bent tip to smoothly exit and regress from the side port (see FIG. 5B). The angle θ (see FIG. 5B) of the bevel may range from about 0° to about 90°, including, 10° to about 90°, about 20° to about 70°, or 40° to about 60°.

The configurations of the distal tube portion 11 of catheter 1 shown in FIGS. 2A-2G allow the catheter 1 to be used as an effective crossing device via subintimal exploration. The advancement of the guide-tip 3 can be effected by rotation of a proximal section of the catheter which transfers a torque to the guide-tip 3, e.g., by a torquing device or handle coupled with an outer sheath of the catheter tubing as will be further described hereinbelow. The rotational advancement of the lateral wings 8a and 8b within the subintimal space can create a more effective delamination of layers of the blood vessel than a symmetrical blunt tip due to the presence of a controlled wide cutting or dissection plane formed by the opposing wings. Moreover, the laterally extending wings 8a/8b can facilitate orienting the catheter 1 in the subintimal space, which in conjunction with the radiopaque markers and the side ports makes it possible for the catheter 1 to also serve as an orienting device, where a pre-biased reentry wire or other type of reentry device can be manipulated and steered via the aid of radiographic visualization (e.g., x-ray fluoroscopy) to exit from one of the side ports toward the true lumen.

As shown in FIGS. 2A and 2C, the tube wall 10 of the distal tube portion 11 of catheter 1 can include a section containing a spiral cut 15 progressing about the longitudinal axis L of the tube. The spiral cut may be made using a laser, e.g., femto-second solid-state cutting laser, by removing tube material from the tube wall. A tube portion having spiral cuts can also be viewed as a ribbon or flat coil (made of portions of the remaining tube wall) wound helically about the longitudinal axis.

A spiral-cut section of the catheter can be used directly within the vasculature and may not require an outer jacket or an inner liner. Alternatively, a spiral cut section can be covered by a jacket 10a, as shown and described in connection in FIGS. 2C and 2F. Also, as shown in FIG. 5A, when located in a spiral-cut section of the distal tube portion 11, the port 6 can have a solid rim 61 that is not breached by the spiral cut 15 (in other words, the spiral cut 15 does not cut through the edge of the side port 6). As shown in FIG. 5B, if the tube wall is covered by a jacket 10a, the outer jacket 10a can be sufficiently removed around the side port so as not to interfere the re-entry wire from exiting or regressing from the side port.

The catheter may have several different spiral-cut patterns, including continuous and discontinuous. The spiral-cut sections may provide for a graduated transition in bending flexibility. For example, the spiral-cut pattern may have a pitch that changes, to increase flexibility in one or more areas. The pitch of the spiral cuts can be measured by the distance between points at the same radial position in two adjacent threads. In one embodiment, the pitch may increase as the spiral cut progresses from a proximal position to the distal end of the catheter. In another embodiment, the pitch may decrease as the spiral cut progresses from a proximal position of the catheter to the distal end of the catheter. In this case, the distal end of the catheter may be more flexible. By adjusting the pitch of the spiral cuts, the pushability, kink resistance, torque, flexibility and compression resistance of the catheter may be adjusted.

Spiral-cut sections having different cut patterns may be distributed along the length of the catheter. The spiral-cut patterns may be continuous or discontinuous along the length of the catheter. For example, there may be 1, 2, 3, 4, 5, 6, 7, . . . , n spiral-cut sections along the length of the catheter, wherein within each section a constant cut pattern may be present but across different sections the cut patterns vary, e.g., in terms of pitch. Each section may also contain a variable pitch pattern within the particular section. Each spiral-cut section may have a constant pitch, e.g., in the range of from about 0.05 mm to about 10 mm, e.g., 0.1 mm, 0.2 mm, 0.3 mm, 0.4 mm, 0.5 mm, 0.6 mm, 0.7 mm, 0.8 mm, 0.9 mm, 1.0 mm, 1.5 mm, 2.0 mm, 3.0 mm, 3.5 mm, 4.0 mm, etc. The pitch may also vary within each section. The pitches for different spiral-cut sections may be same or different. Alternatively, the catheter may have a continuously changing spiral-cut pattern along the length of the catheter. The orientation or handedness of spiral-cut sections in the catheter may also vary among spiral-cut sections.

Figure 6:
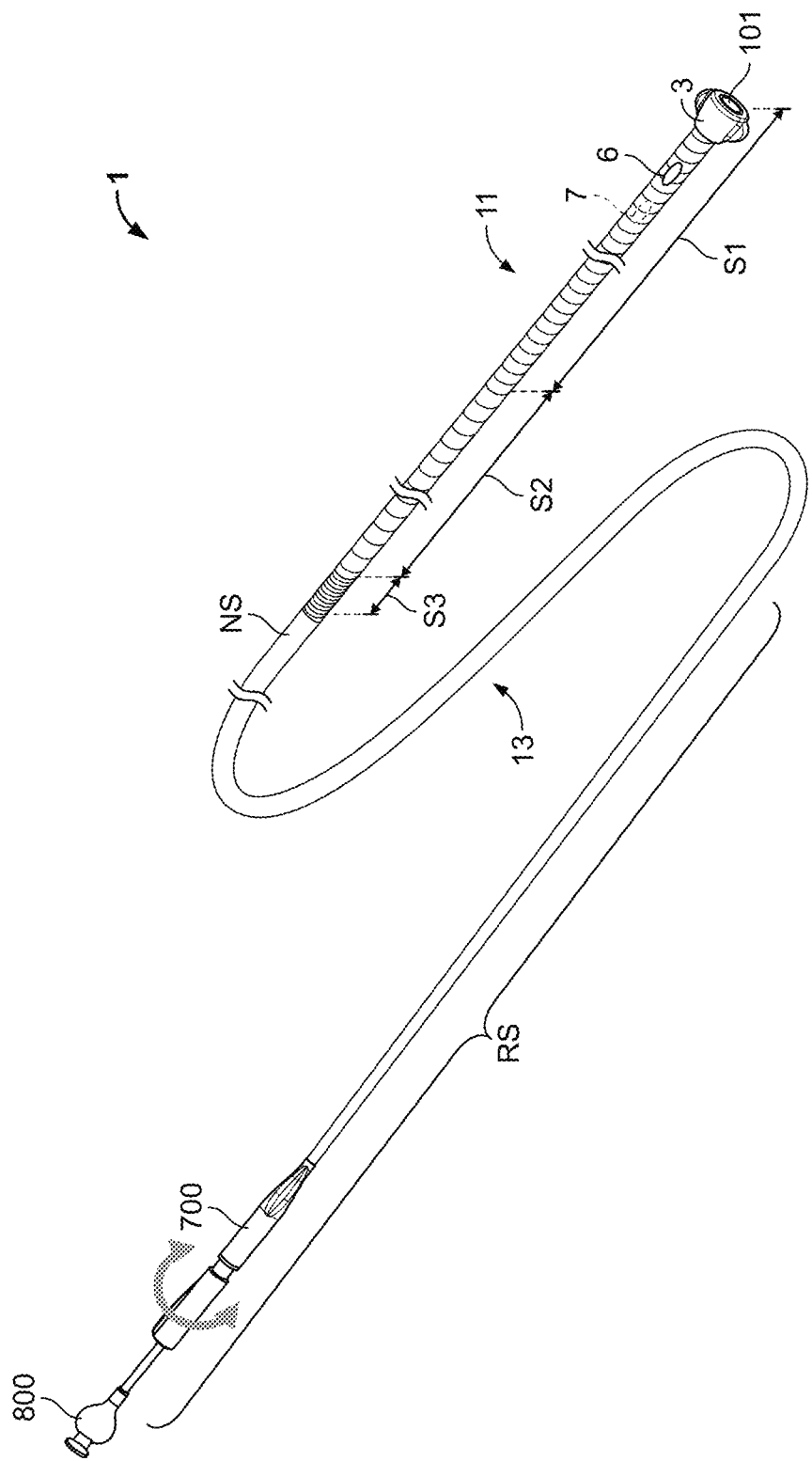
FIG. 6 shows a catheter containing a plurality of spiral-cut sections on a distal catheter tube portion according to some embodiments of the present invention.

As graphically illustrated in FIG. 6 which shows a catheter 1 having a distal tube portion 11 including three consecutive spiral-cut sections, S1, S2, and S3, along its length direction. Section S1 is located at the distal end of the catheter 1, and can include a guide-tip 3 at the distal end 101 of the catheter, as well as two radially opposite and longitudinally offset side ports 6 and 7. All three spiral-cut sections can be made from a same tube (e.g., a hypotube) having a constant diameter. The distal tube portion 11 can also include an uncut portion NS proximal to spiral-cut section S3. Catheter 1 further includes a proximal tube portion 13, which can be fabricated from the same tube as distal tube portion 11, or constructed from a different tube and joined with distal tube portion 11. The proximal tube portion 13 is connected to a proximal tab 800 located at the proximal end of the catheter 1, and runs through a handle assembly or torquing device 700, as described herein. The proximal tube portion 13 can also include a section RS which has a non-circular cross section shape (also referred to as a "railed" section, as described hereinafter) for engagement with the handle assembly 700.

Spiral sections S1, S2, S3 may each have a length and a pitch to provide a dimension and flexibility for the intended use of the catheter. For example, the lengths and pitches for each section may be selected for the performance requirements (e.g., diameter, length, shape and other configurations of the vasculature to be navigated by the catheter for accessing the treatment site) for performing a specific procedure, such as an antegrade CTO PCI procedure. For example, in one embodiment, section S1 can have a length ranging from about 10 cm-15 cm and a pitch ranging from about 0.5 mm to about 1.0 mm, section S2 can have a length ranging from about 4 to about 6 cm and a pitch ranging from about 1 to about 2 mm, section S3 can have a length ranging from about 0.5 cm to about 2 cm and a pitch ranging from 0.05 mm to about 0.3 mm.

Figure 7A:
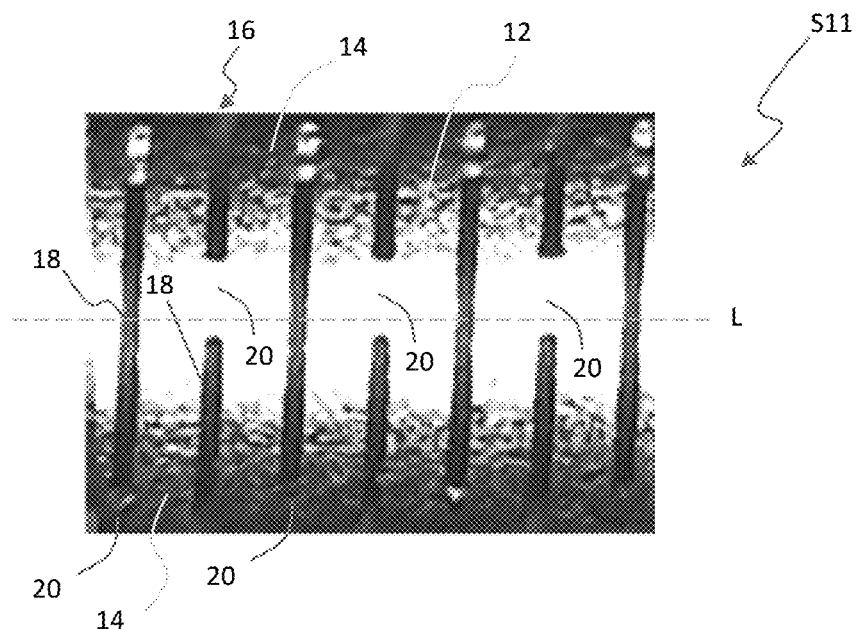
FIG. 7A is a side view of spiral-cut section of a catheter including interrupted spirals according to an embodiment of the present invention.
Figure 7B:
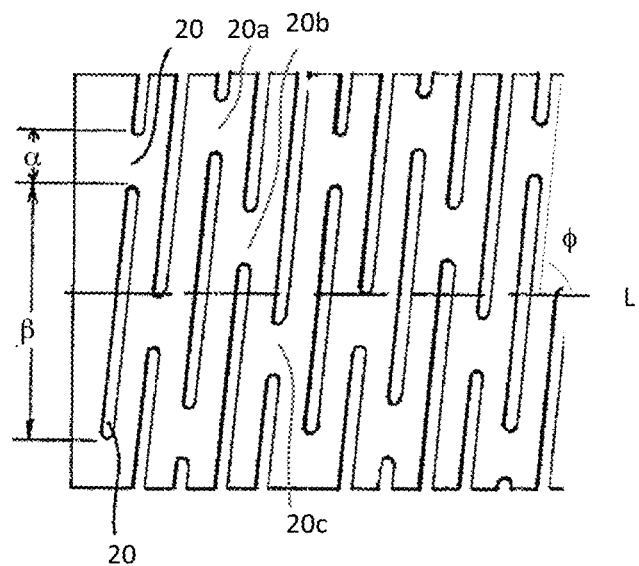
FIG. 7B depicts a section of a catheter having an interrupted spiral-cut pattern in an unrolled condition according to one embodiment of the present invention.
Figure 8A:
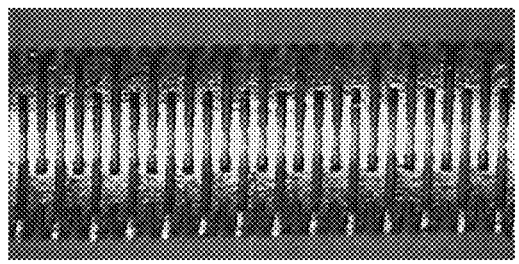
FIGS. 8A-8D are photographs of different spiral-cut portions of a catheter according to an embodiment of the present invention.
Figure 8B:
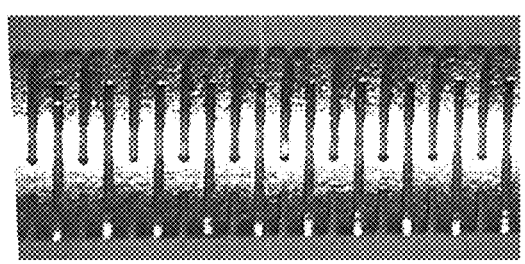
Figure 8C:
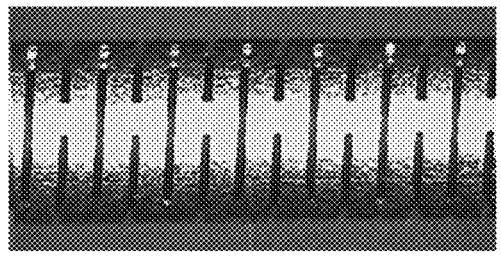
Figure 8D:

The above illustrated spiral-cuts are continuous in the spiral-cut sections. Additionally, the spiral-cuts can include a pattern of interrupted spirals, i.e., spirals that include both cut and uncut portions. As illustrated in FIGS. 7A and 7B, a spiral-cut tube section S11 of a catheter with a spiral ribbon 12 having adjacent turns 14 which are substantially defined and separated by an interrupted spiral 16, which includes alternating open or cut portions 18 and uncut portions 20. The pathway of the alternating cut and uncut sections 18 and 20 is angled with respect to a circumference of the tube portion (in other words, the pitch angle φ shown in FIG. 7B is smaller than 90 degrees). The presence of the uncut portions 20 makes the tube portion more stretch resistant than a typical wound ribbon or continuously spiral-cut tube.

Similar to what has been described with respect to continuous spiral-cuts herein, an interrupted spiral-cut pattern can also have a varying pitch that decreases from a relatively rigid region to a relatively flexible region. When a side port 6 such as one illustrated in connection with FIGS. 2A/5A is located in an interrupted spiral-cut section instead of a continuous spiral shown in FIGS. 2A/5A, the port 6 can also have a solid rim not breached by interrupted spiral cuts.

As illustrated in FIG. 7B, which depicts a portion of an unrolled catheter tube with an interrupted spiral-cut pattern, where each helically oriented uncut portion 20 has an arcuate extent "α", and each helically oriented cut portion 18 has an arcuate extent "β". α and β can be expressed in degrees (where each complete helical turn is 360°). The uncut portions can be distributed such that adjacent uncut portions 20 (20a, 20b, 20c) are not in axial alignment (or "staggered") with each other along a direction parallel to the longitudinal axis L. Alternatively, uncut portions in successive helical turns can be in axial alignment to render the tube section with a bending bias. Further alternatively, as shown in FIG. 7A, the uncut portions 20 on every other turn of the interrupted spiral 16 can be axially aligned.

In some embodiments, for an interrupted spiral-cut section, the interrupted spiral pattern can be designed such that each turn or rotation of the spiral includes a specific number of cuts, Nc (e.g., 1.5, 2.5, 3.5, 4.5, 5.5, etc.). Nc can also be whole numbers, such as 2, 3, 4, 5, . . . , n, as well as other real numbers, such as 2.2, 2.4, 2.7, 3.1, 3.3, etc. At a given Nc, the uncut extent α and the cut extent β can be chosen as α=(360−(β*Nc))/Nc such that each rotation has Nc number of repeat patterns each comprising a cut portion of extent β adjacent an uncut portion of extent α. For example, at Nc=1.5, 2.5, and 3.5, the following table shows example choices of various embodiments for α and β:

| Nc = 1.5 | | Nc = 2.5 | | Nc = 3.5 | |
| --- | --- | --- | --- | --- | --- |
| β (°) | α (°) | β (°) | α (°) | β (°) | α (°) |
| 230 | 10 | 140 | 4 | 90 | 12.85714286 |
| 229 | 11 | 139 | 5 | 89 | 13.85714286 |
| 228 | 12 | 138 | 6 | 88 | 14.85714286 |
| 227 | 13 | 137 | 7 | 87 | 15.85714286 |
| 226 | 14 | 136 | 8 | 86 | 16.85714286 |
| 225 | 15 | 135 | 9 | 85 | 17.85714286 |
| 224 | 16 | 134 | 10 | 84 | 18.85714286 |
| 223 | 17 | 133 | 11 | 83 | 19.85714286 |
| 222 | 18 | 132 | 12 | 82 | 20.85714286 |
| 221 | 19 | 131 | 13 | 81 | 21.85714286 |
| 220 | 20 | 130 | 14 | 80 | 22.85714286 |
| 219 | 21 | 129 | 15 | 79 | 23.85714286 |
| 218 | 22 | 128 | 16 | 78 | 24.85714286 |
| 217 | 23 | 127 | 17 | 77 | 25.85714286 |
| 216 | 24 | 126 | 18 | 76 | 26.85714286 |
| 215 | 25 | 125 | 19 | 75 | 27.85714286 |
| 214 | 26 | 124 | 20 | 74 | 28.85714286 |
| 213 | 27 | 123 | 21 | 73 | 29.85714286 |
| 212 | 28 | 122 | 22 | 72 | 30.85714286 |
| 211 | 29 | 121 | 23 | 71 | 31.85714286 |
| 210 | 30 | 120 | 24 | 70 | 32.85714286 |
| 209 | 31 | 119 | 25 | 69 | 33.85714286 |

-continued

| Nc = 1.5 | | Nc = 2.5 | | Nc = 3.5 | |
|---|---|---|---|---|---|
| β (°) | α (°) | β (°) | α (°) | β (°) | α (°) |
| 208 | 32 | 118 | 26 | 68 | 34.85714286 |
| 207 | 33 | 117 | 27 | 67 | 35.85714286 |
| 206 | 34 | 116 | 28 | 66 | 36.85714286 |
| 205 | 35 | 115 | 29 | 65 | 37.85714286 |

FIGS. 8A-8D are photographs of portions of a tube having interrupted spiral cuts with different pitches, as described herein.

The catheter of the present invention can include continuous spiral-cut sections (as those illustrated in FIG. 2A, 2C, 2F, 6) interrupted spiral cut sections (as those illustrated in FIGS. 7A-7C), or a hybrid of both types of spiral-cut patterns, arranged in any order.

To facilitate the transversal of a distal portion of the catheter tube 1 in the blood vessel of a subject, a torquing device (or handle assembly) can be provided to attach to a proximal portion of the catheter tube. The handle assembly can include a lumen or internal opening to accommodate the catheter tube, as well as to frictionally engage the catheter tube to apply a torque when a portion of the handle assembly is rotated.

Figure 9A:
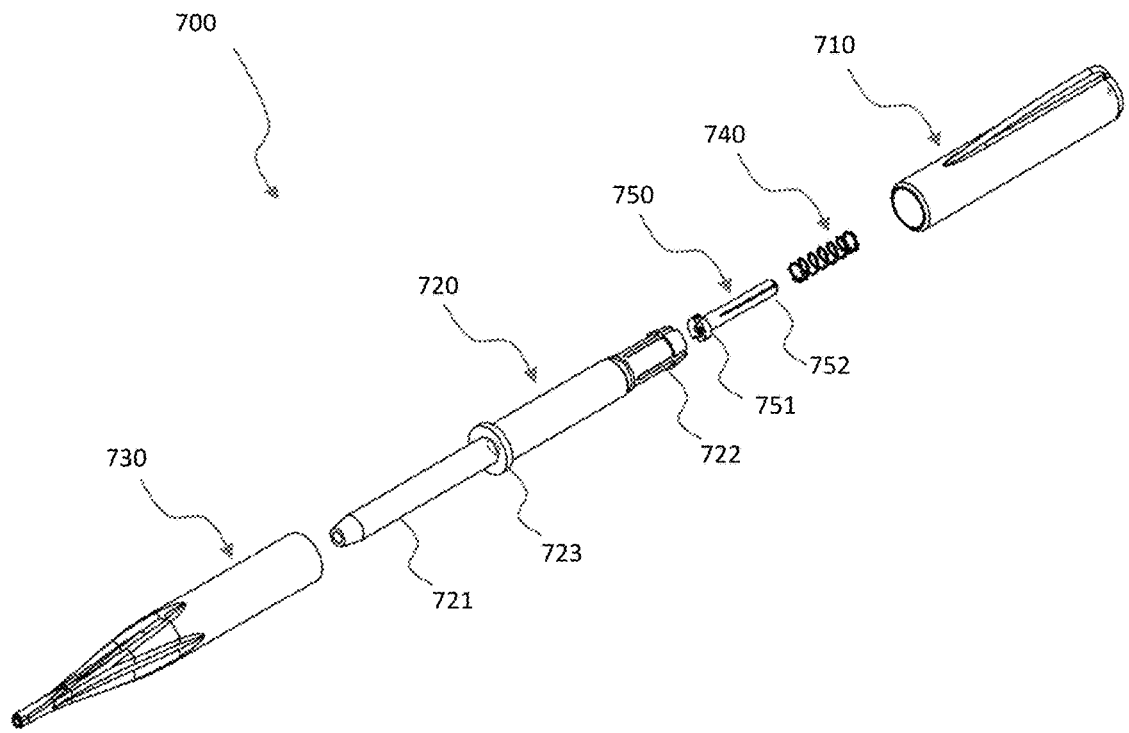
FIG. 9A is an exploded view of components of a handle assembly for use with a catheter according to some embodiments of the present invention.
Figure 9B:
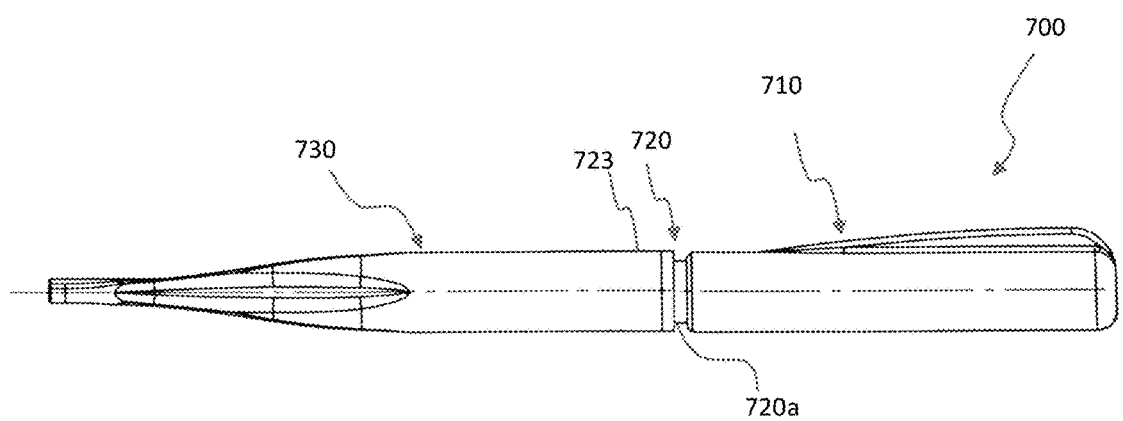
FIG. 9B depicts the handle assembly as assembled in a first configuration from the components shown in FIG. 9A.

In one embodiment, and as illustrated in FIGS. 9A-9B, a handle assembly 700 includes a proximal sleeve 710, a distal outer grip 720 (which includes a distal portion 721, a proximal portion 722, and a flange 723 disposed between distal portion 721 and proximal portion 722), a distal grip sleeve 730, a spring 740, and a chuck 750 (which includes a distal flange 751 and a proximal portion 752). Each of the proximal sleeve 710, chuck 750, and distal outer grip 720 at least includes a through lumen with sufficient cross section area to allow a proximal portion 13 of catheter 1 to pass through. Additionally, the proximal sleeve 710 has a second lumen to accommodate a portion of the distal outer grip 720, and a third lumen to accommodate a portion of chuck 750. Further, the proximal portion 722 of the distal outer grip 720 includes a second lumen with a diameter to enclose the chuck 750 (including the flange 751). The spring 740 has an axial length smaller than that of the proximal portion 752 of the chuck 750, a diameter greater than that of the proximal portion 752 of the chuck 750 but smaller than the diameter of the distal flange 751 of the chuck 750.

The handle assembly 700 as assembled is shown in FIG. 9B, where the distal portion 721 of the distal outer grip 720 is covered by the distal grip sleeve 730, while the flange 723 remains visible. The proximal portion 752 of the chuck 750 is encircled by the coils of the spring 740. The chuck 750 and the spring 740 are accommodated inside the second lumen of the distal outer grip 720 as well as the third lumen of the proximal sleeve 710. The proximal sleeve 710 covers most of the proximal portion 722 of the distal outer grip 720. A short segment 720a proximal to the flange 723 of the distal outer grip 720 is exposed. This configuration shown in FIG. 9B is also referred to as a "locked" position where relative rotation of the proximal sleeve 710 and the distal grip sleeve 730 can create controlled advancement or withdrawal of the catheter within the patient's vasculature. Such rotation can be accomplished by an operator using one hand or using both hands.

Figure 9C:
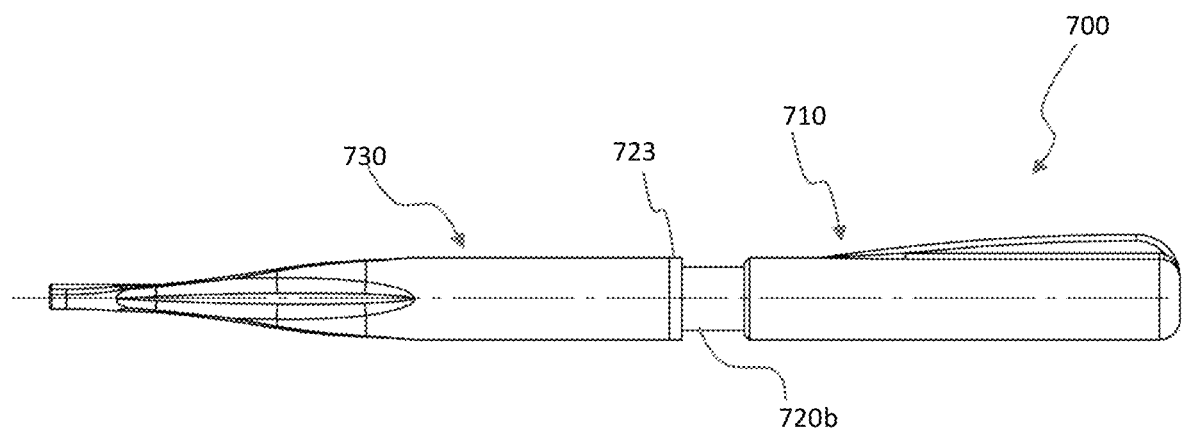
FIG. 9C depicts the handle assembly as assembled in a second configuration from the components shown in FIG. 9A.

Compared to known catheter systems where a torquing handle is located at a fixed proximal position of the catheter tube, an advantage of the handle assembly of the present invention as illustrated herein is that the handle assembly can be easily unlocked or disengaged from the catheter tube so that the operator can slide the handle assembly to a different position of the catheter tube where the handle assembly can be relocked or re-engaged with the catheter tube. For example, after passing a length of the catheter tube into the vasculature of the patient, the handle assembly can be unlocked by pulling the proximal sleeve 710 away from the distal outer grip 720, resulting in an unlocked configuration where the exposed section 720b is greater than that of 720a, as shown in FIG. 9C. In this unlocked configuration, the handle assembly 700 can be slid as a whole along the railed section of the catheter to a more distal position on the catheter (i.e., further away from the proximal tab 800 and closer to the entry point of the catheter into the body of the patient), where it can be relocked by reverting back to the configuration shown in FIG. 9B. This capability of repositioning the handle assembly on different points on the catheter allows the handle assembly to be kept at a point close to the patient body, which reduces the distance between the distal tip of the catheter and the point where the torque is applied, thereby allowing for more effective transfer of torque from the point where the torque is applied to the distal tip of the catheter.

Figure 10A:
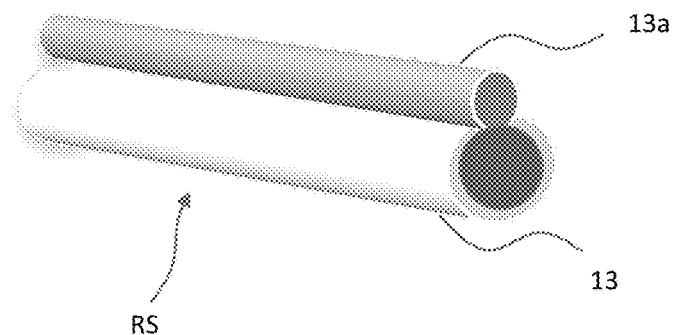
FIG. 10A depicts a configuration of a proximal portion of a catheter according to some embodiments of the present invention.

To enhance the frictional engagement between the handle assembly and the catheter and to facilitate transfer of torque from the handle assembly, a portion of the proximal tube portion 13 of the catheter can be modified to have a cross section shape that deviates from a general circular cross section shape. For example, as shown in FIG. 10A, a length of a wire or tube (either solid or hollow) 13a can be attached outside of a portion of the proximal catheter tube portion 13. The portion of the catheter tube having the attached wire or tube 13a is also referred to as a "railed" section (RS), as previously noted. The wire or tube 13a can have a size or diameter smaller than that of the proximal catheter tube portion 13, e.g., from about 5% to about 50% of the diameter of the proximal catheter tube portion 13. Alternatively, a section of the proximal portion of the catheter can be modified such that it has a non-circular cross section, in which case an externally attached wire or tube may not be needed.

As shown in FIG. 13C, the cross section of the wire or tube 13a (including 13a1, 13a2, and 13a3) can be circular (13a1) or non-circular, e.g., rectangular (13a2) or triangular (13a3), as well as other shapes, such as semi-circular, elliptical, pentagonal, or hexagonal shape, etc. The attachment between the wire or tube (13a1, 13a2, and 13a3) and the catheter tube portion 13 can be effected by providing a shrink wrapping (13b1, 13b2, 13b3) that securely encloses both the wire or tube 13a and the proximal catheter portion 13.

Figure 10B:
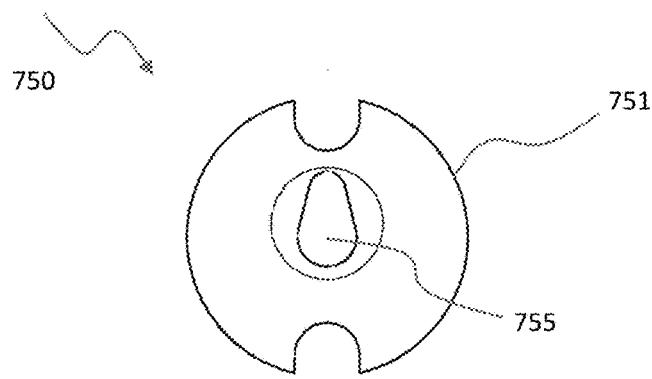
FIG. 10B is a front view of a component of the handle assembly shown in FIG. 9A.
Figure 10C:
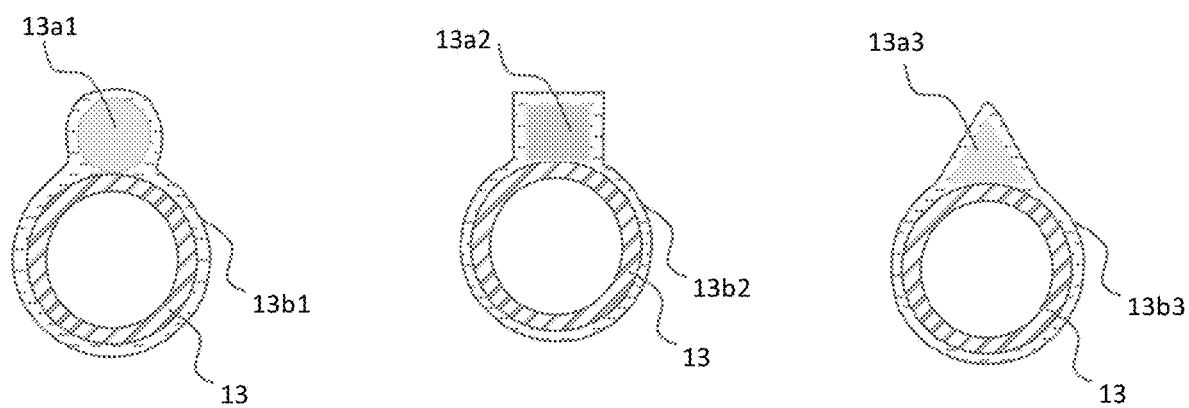
FIG. 10C depicts various cross section configurations of a proximal portion of a catheter according to some embodiments of the present invention.

To accommodate the railed section of the catheter, an internal lumen of the chuck 750 and of the proximal sleeve 710 of the handle assembly can take a corresponding cross sectional shape. For example, as illustrated in FIG. 10B, which is a front view of the chuck 750 (the front face of flange 751 is visible), where a lumen 755 for accommodating the railed section of the catheter is shown to have a shape and size that can slidably fit the overall cross section shape and size of the railed section as shown in FIG. 10A. The lumen 755 can also be shaped and sized to slidably fit any of the cross sections of the shrink wrappings 13b1, 13b2, or 13b3, as shown in FIG. 10C.

The catheter device of the present invention may be used to facilitate treatment of CTO lesions, such as in the coronary artery of a patient. First, a catheter of the present invention with a guide-tip having at least one wing (e.g., having two radially opposed wings) and a side port in a distal tube portion is advanced in the blood vessel and approaches the CTO lesion (or occlusion) in an artery. Then, the guide-tip of the catheter is advanced through the intima of the artery in a distal direction, until the at least one side port reaches a position in the subintimal space distal to the CTO lesion. In this process, the guide-tip causes dissection of the layers forming the wall of artery and establishes a channel extending longitudinally across the CTO lesion. The at least one side port can be oriented toward the true vascular lumen. Subsequently, while the guide-tip is retained in the subintimal space, a re-entry wire or device with a pre-biased distal tip portion can be introduced into the lumen of the catheter in a compressed state, and manipulated such that the distal tip of the re-entry wire or device exits from the at least one side port in a natural (uncompressed) state with the aid of radiographic visualization and enter into the true lumen.

Figure 11:
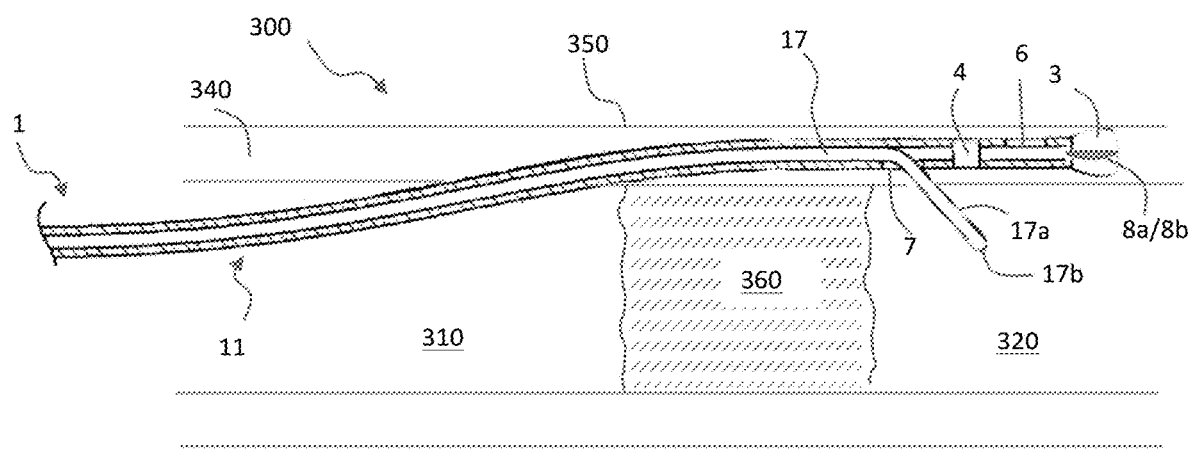
FIG. 11 depicts a configuration of a catheter after passing a CTO lesion from the subintimal space and a re-entry device reentering the vascular lumen from a side port of the catheter according to some embodiments of the present invention.

FIG. 11 depicts the final stage of this process. In the section of artery 300 having a vascular wall 350, the occlusion 360 separates the vascular lumen into a proximal segment 310 and a distal segment 320. The distal tube portion 11 of a catheter 1 has been advanced in the subintimal space 340 and a proximal side port 6 (as well as a distal side port 7) of the catheter has been advanced past the position of the occlusion 360. Radially opposed wings 8a/8b (as those shown in FIG. 2A) on the guide-tip are oriented circumferential with the vascular wall 350. The side port 6 faces toward the distal segment of vascular lumen 320. The distal tip 17b of the re-entry device 17 with a pre-biased tip portion 17a has exited from side port 7 and into the distal segment 320 of the vascular lumen with the aid of radiopaque marker 4. The distal tip 17b of the re-entry device may include a highly radiopaque material enabling it to be visualized within the catheter lumen while advancing or withdrawing the wire as well as visually enabling the operator to choose and guide the reentry wire from the correct orientation out of the side ports under fluoroscopic guidance.

In the above approach where the re-entry device or wire having a pre-biased tip is introduced into the true lumen via a side port, one or more side ports may be utilized during the reentry manipulation. For example, for a catheter having two radially opposed side ports and two corresponding radiopaque markers as illustrated in FIG. 2A, the reentry wire may be introduced into the true lumen by a first attempt to penetrate the pre-biased tip of the re-entry wire through either side port. If the first attempt is not successful, the re-entry wire is withdrawn from that side port and a second attempt can be made to manipulate the tip of the reentry device to exit from the other side port while maintaining the position and orientation of the wings of the catheter. The second attempt is expected to be successful because the orientation of the exit ports is such that one exit port faces toward the true lumen and the other faces the opposite side. Such reentry can also be accomplished using only one side port, where if the first attempt is unsuccessful, the catheter can be rotated for about 180 degrees within the subintimal space to arrive at another stable position, and the reentry is attempted again, which is expected to be successful. The radiopaque markers illustrated in connection with FIGS. 4A and 4B can also be used to determine the orientation of the catheter and the side ports for manipulation of the reentry wire to enter into the true lumen.

The scope of the present invention is not limited by what has been specifically shown and described hereinabove. Those skilled in the art will recognize that there are suitable alternatives to the depicted examples of configurations, constructions, and dimensions, and materials. The citation and discussion of any references in the application is provided merely to clarify the description of the present invention and is not an admission that any reference is prior art to the invention described herein. All references cited and discussed in this specification are incorporated herein by reference in their entirety. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A catheter device comprising:
a distal tube portion having a longitudinal axis and a tube wall comprising at least one side port; and
a guide tip mounted on the distal tube portion, the guide tip defining:
a unitary body having an outer wall, and
a plurality of fixed wings that are an integral part of the unitary body and immovable with respect thereto, wherein each wing extends radially outward from a portion of the outer wall, and wherein each wing defines an edge co-planar with a distal-most end of the guide tip, wherein the catheter device includes at least one spiral-cut section, and wherein the at least one side port is located in the spiral-cut section and includes a rim not breached by a spiral cut.

2. A catheter device comprising:
a distal tube portion having a longitudinal axis and a tube wall comprising at least one side port; and
a guide tip mounted on the distal tube portion, the guide tip defining:
a unitary body having an outer wall, and
a plurality of fixed wings that are an integral part of the unitary body and immovable with respect thereto, wherein each wing extends radially outward from a portion of the outer wall, and wherein each wing defines an edge co-planar with a distal-most end of the guide tip, further comprising a radiopaque marker affixed on the distal tube portion in axial alignment with the at least one side port.

3. A catheter device comprising:
a distal tube portion having a longitudinal axis and a tube wall comprising at least one side port; and
a guide tip mounted on the distal tube portion, the guide tip defining:
a unitary body having an outer wall, and
a plurality of fixed wings that are an integral part of the unitary body and immovable with respect thereto, wherein each wing extends radially outward from a portion of the outer wall, and wherein each wing defines an edge co-planar with a distal-most end of the guide tip, further comprising a radiopaque marker encircling the at least one side port.

4. The catheter device of claim 1, wherein each of the plurality of wings defines an axial length smaller than an overall axial length of the guide tip.

5. The catheter device of claim 1, wherein the plurality of wings includes 4 or more equally-spaced wings.

6. The catheter device of claim 1, wherein the at least one side port is radially offset from each of the plurality of wings.

7. The catheter device of claim 1, wherein a height of each of the plurality of wings ranges from about 5% to about 50% of an outer diameter of the guide tip.

8. The catheter device of claim 2, wherein each of the plurality of wings defines an axial length smaller than an overall axial length of the guide tip.

9. The catheter device of claim 2, wherein the plurality of wings includes 4 or more equally-spaced wings.

10. The catheter device of claim 2, wherein the at least one side port is radially offset from each of the plurality of wings.

11. The catheter device of claim 2, wherein a height of each of the plurality of wings ranges from about 5% to about 50% of an outer diameter of the guide tip.

12. The catheter device of claim 3, wherein each of the plurality of wings defines an axial length smaller than an overall axial length of the guide tip.

13. The catheter device of claim 3, wherein the plurality of wings includes 4 or more equally-spaced wings.

14. The catheter device of claim 3, wherein the at least one side port is radially offset from each of the plurality of wings.

15. The catheter device of claim 3, wherein a height of each of the plurality of wings ranges from about 5% to about 50% of an outer diameter of the guide tip.

\* \* \* \* \*